(12) United States Patent
Caldarise et al.

(10) Patent No.: US 9,046,699 B2
(45) Date of Patent: *Jun. 2, 2015

(54) DYNAMIC FLUID ZONES IN CONTACT LENSES

(75) Inventors: Salvatore G. Caldarise, St. Johns, FL (US); Jeffrey H. Roffman, Saint Johns, FL (US); Lenora L. Copper, Jacksonville, FL (US); Ryan Hawke, Jacksonville, FL (US); Daniel B. Otts, Fruit Cove, FL (US)

(73) Assignee: JOHNSON & JOHNSON VISION CARE, INC., Jacksonville, FL (US)

( * ) Notice: Subject to any disclaimer, the term of this patent is extended or adjusted under 35 U.S.C. 154(b) by 263 days.

This patent is subject to a terminal disclaimer.

(21) Appl. No.: 13/418,661

(22) Filed: Mar. 13, 2012

(65) Prior Publication Data

US 2013/0242255 A1 Sep. 19, 2013

(51) Int. Cl.
*G02C 7/04* (2006.01)

(52) U.S. Cl.
CPC . *G02C 7/04* (2013.01); *G02C 7/048* (2013.01)

(58) Field of Classification Search
CPC .......... G02C 7/04; G02C 7/048; G02C 7/049
USPC .............. 351/159.01–159.04, 159.73–159.74
See application file for complete search history.

(56) References Cited

U.S. PATENT DOCUMENTS

| 4,477,158 | A | 10/1984 | Pollock et al. |
| 4,702,573 | A | 10/1987 | Morstad |
| 5,788,957 | A | 8/1998 | Harris |
| 7,452,075 | B2 | 11/2008 | Iuliano |
| 7,559,650 | B2 | 7/2009 | Iuliano |
| 7,699,464 | B2* | 4/2010 | Iuliano ..................... 351/159.34 |
| 7,878,650 | B2 | 2/2011 | Fritsch et al. |
| 2004/0150787 | A1* | 8/2004 | Niculas et al. ............ 351/160 R |
| 2005/0094094 | A1 | 5/2005 | Asher |
| 2006/0290882 | A1* | 12/2006 | Meyers et al. ............ 351/160 H |
| 2007/0153231 | A1 | 7/2007 | Ivliano |
| 2009/0190091 | A1 | 7/2009 | Wright et al. |
| 2010/0245760 | A1 | 9/2010 | Win-Hall |
| 2012/0206692 | A1 | 8/2012 | Yamaguchi et al. |

FOREIGN PATENT DOCUMENTS

| DE | 2426757 A | 12/1975 |
| EP | 0390443 | 10/1990 |
| EP | 159941 A2 | 12/2001 |

(Continued)

OTHER PUBLICATIONS

Efron, N., et al. "Contact Lens Practice (Stabilization Techniques of Soft Toric Lenses", XP55065013, Butterworth Heinemann Elsevier, p. 120-121 (2010).
European Search Report completed Jun. 6, 2013 for corresponding Application No. EP13159040.
European Search Report completed Jun. 5, 2013 for corresponding Application No. EP13159058.

(Continued)

*Primary Examiner* — Ricky Mack
*Assistant Examiner* — Robert E Tallman
(74) *Attorney, Agent, or Firm* — Carl J. Evens

(57) ABSTRACT

A contact lens incorporating one or more dynamic fluid zones fabricated from a material that is readily deformable under eyelid pressure during blinking allows for the delivery of one or more agents to the eye, dynamic cosmetic eye enhancement, and/or dynamic rotational misalignment correction. The one or more agents may include therapeutic agents, nutritional agents and pharmacological agents.

41 Claims, 8 Drawing Sheets

(56) References Cited

FOREIGN PATENT DOCUMENTS

| GB | 2464981 A | 5/2010 |
|---|---|---|
| WO | WO 91/10154 A1 | 7/1991 |
| WO | WO 02/27388 A1 | 4/2002 |
| WO | WO 2008/115251 A1 | 9/2008 |
| WO | WO 2011/061790 A1 | 8/2012 |

OTHER PUBLICATIONS

Search Report for corresponding Singapore Patent Application No. 201300811-5 dated Apr. 17, 2013.
Patent Examination Report issued by the Australian Patent Office dated Dec. 20, 2013 for corresponding Application No. 2013201260.
European Search Report for Application. No. EP13159040 dated Sep. 23, 2013.

* cited by examiner

DYNAMIC FLUID ZONES IN CONTACT LENSES

BACKGROUND OF THE INVENTION

1. Field of the Invention

The present invention relates to dynamic fluid/gel zones for contact lenses, and more particularly to contact lenses incorporating one or more dynamic fluid/gel zones that may be utilized for one or both of delivering one or more therapeutic, nutritional or pharmacological agents, and dynamic, cosmetic eye enhancement.

2. Discussion of the Related Art

Myopia or nearsightedness is an optical or refractive defect of the eye wherein rays of light from an image focus to a point before they reach the retina. Myopia generally occurs because the eyeball or globe is too long or the cornea is too steep. A minus powered spherical lens may be utilized to correct myopia. Hyperopia or farsightedness is an optical or refractive defect of the eye wherein rays of light from an image focus to a point after they reach or behind the retina. Hyperopia generally occurs because the eyeball or globe is too short or the cornea is too flat. A plus powered spherical lens may be utilized to correct hyperopia. Astigmatism is an optical or refractive defect in which an individual's vision is blurred due to the inability of the eye to focus a point object into a focused image on the retina. Unlike myopia and/or hyperopia, astigmatism has nothing do to with globe size or cornea steepness, but rather it is caused by an abnormal curvature of the cornea. A perfect cornea is spherical whereas in an individual with astigmatism, the cornea is not spherical. In other words, the cornea is actually more curved or steeper in one direction than another, thereby causing an image to be stretched out rather than focused to a point. A cylindrical lens rather than a spherical lens may be utilized to resolve astigmatism.

A toric lens is an optical element having two different powers in two orientations that are perpendicular to one another. Essentially, a toric lens has one power, spherical, for correcting myopia or hyperopia and one power, cylinder, for correcting astigmatism built into a single lens. These powers are created with curvatures at different angles which are preferably maintained relative to the eye. Toric lenses may be utilized in eyeglasses, intraocular lenses and contact lenses. The toric lenses used in eyeglasses and intraocular lenses are held fixed relative to the eye thereby always providing optimal vision correction. However, toric contact lenses may tend to rotate on the eye thereby temporarily providing sub-optimal vision correction. Accordingly, toric contact lenses also include a mechanism to keep the contact lens relatively stable on the eye when the wearer blinks or looks around.

In order to treat infection, inflammation, glaucoma, and other ocular diseases, drugs are often required to be administered to the eye. A conventional method of drug delivery is by topical application to the eye's surface. The eye is uniquely suited to this surface route of drug administration because, properly constituted, drugs can penetrate through the cornea, rise to therapeutic concentration levels inside the eye, and exert their beneficial effects. In practice, eye drops currently account for more than ninety-five (95) percent of drug delivery methods for the eye. Rarely are drugs for the eye administered orally or by injection, either because they reach the eye in too low a concentration to have the desired pharmacological effect, or because their use is complicated by significant systemic side effects.

Eye drops, though effective, are unrefined and inefficient. When an eye drop is instilled in the eye, it typically overfills the conjuctival sac, the pocket between the eye and the eyelids, causing a substantial portion of the drop to be lost due to overflow of the eyelid margin onto the cheek. In addition, a substantial portion of the drop remaining on the ocular surface is washed away by tears into the tear drainage system, thereby diluting the concentration of the drug. Not only is this share of the drug dose lost before it can cross the cornea, but this excess drug may be carried into the nose and throat where it is absorbed into the general circulation, sometimes leading to serious systemic side effects. The small portion of the drug in the eye drop which does penetrate the cornea results in an initial peak tissue concentration, a higher level than is required for the initial pharmacological effect. This tissue concentration then gradually decreases, such that by the time the next eye drop is due, the tissue concentration and the intended pharmacological effect may be too low.

To compound the problems described above, patients often do not use their eye drops as prescribed. Often, this poor compliance is due to an initial stinging or burning sensation caused by the eye drop. Certainly, instilling eye drops in one's own eye can be difficult, in part because of the normal reflex to protect the eye. Older patients may have additional problems instilling drops due to arthritis, unsteadiness, and decreased vision, and pediatric and psychiatric patient populations pose difficulties as well. Accordingly, contact lenses may provide a viable means for solving the problems of reliable and efficient drug delivery to the eye.

The use of tinted or colored contact lenses to alter or enhance the natural color of the iris is well known. In manufacturing conventional tinted contact lenses, it is known to use either or both translucent and opaque colors in one layers of color with the object of creating a natural appearing tinted iris. Typically, the color layers are each applied at a single thickness. This provides color variation only with the use of multiple colors or points at which the translucent color overlaps another color layer. However, the natural iris is composed of a large number of different colors and color combinations intermixed to create color variations. The relatively small number of colors and color layers that may be utilized in producing tinted contact lenses limits the designer's ability to create a natural appearing lens. Accordingly, it would be advantageous to create a form of dynamic eye color enhancement above simply altering the color of the iris.

Accordingly, it would be advantageous to design a contact lens with dynamic stabilization zones that auto-position the contact lens quickly and hold and/or maintain the desired position for optimal visual acuity regardless of eye movement, blinking and tears. It would also be advantageous to design a contact lens to deliver one or more therapeutic, nutritional or pharmacological agents to the eye. It would also be advantageous to provide dynamic, cosmetic eye enhancement utilizing contact lenses.

SUMMARY OF THE INVENTION

The dynamic fluid zones in contact lenses of the present invention overcome a number of disadvantages associated with prior art contact lenses as briefly described above.

In accordance with one aspect, the present invention is directed to an ophthalmic device. The device comprising a corrective lens having an optic region, a peripheral region surrounding the optic region, a front surface and a back surface, and at least one dynamic fluid zone incorporated into the contact lens between the front surface and the back surface in the peripheral region, the at least one dynamic fluid zone being formed from a deformable material and comprising at least one of a therapeutic, a nutritional, and a pharmacological agent for delivery to an eye of a patient through one or more openings, the at least one dynamic fluid zone being configured to interact with the eyelids such that blinking causes movement of the at least one of a therapeutic, a nutritional, and a pharmacological agent.

In accordance with another aspect, the present invention is directed to an ophthalmic device. The device comprising a corrective lens having an optic region, a peripheral region surrounding the optic region, a front surface and a back surface, and at least one dynamic fluid zone incorporated into the contact lens between the front surface and the back surface in the peripheral region, the at least one dynamic fluid zone being formed from a deformable material and comprising a cosmetically eye enhancing material, the at least one dynamic fluid zone being configured to interact with eyelids such that blinking causes the cosmetically eye enhancing material to move thereby reflecting light in a dynamic manner.

In accordance with yet another aspect, the present invention is directed to an ophthalmic device. The device comprising a contact lens having an optic region, a peripheral region surrounding the optic region, a front surface and a back surface and requiring rotational stability on eye, at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material at eye temperature, and wherein the eyelids make an angle of contact with the at least one dynamic stabilization zone that changes when the eyelids move across the at least one dynamic stabilization zone, and at least one dynamic fluid zone incorporated into the contact lens between the front surface and the back surface in the peripheral region, the at least one dynamic fluid zone being formed from a deformable material and comprising at least one of a therapeutic, a nutritional, and a pharmacological agent for delivery to an eye of a patient through one or more openings, the at least one dynamic fluid zone being configured to interact with the eyelids such that blinking causes movement of the at least one of a therapeutic, a nutritional, and a pharmacological agent.

In accordance with still another aspect, the present invention is directed to an ophthalmic device. The device comprising a contact lens having an optic region, a peripheral region surrounding the optic region, a front surface and a back surface and requiring rotational stability on eye, and at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material, and wherein the eyelids make an angle of contact with the at least one dynamic stabilization zone that changes when the eyelids move across the at least one dynamic stabilization zone, the at least one dynamic stabilization zone also comprising a cosmetically eye enhancing material, the at least one dynamic stabilization zone being configured to interact with the eyelids such that blinking causes the cosmetically eye enhancing material to move thereby reflecting light in a dynamic manner.

In accordance with still yet another aspect, the present invention is directed to an ophthalmic device. The device comprising a contact lens having an optic region, a peripheral region surrounding the optic region, a front surface and a back surface and requiring rotational stability on eye, at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material at eye temperature, and wherein the eyelids make an angle of contact with the at least one dynamic stabilization zone that changes when the eyelids move across the at least one dynamic stabilization zone, and at least one dynamic fluid zone incorporated into the contact lens between the front surface and the back surface in the peripheral region, the at least one dynamic fluid zone being formed from a deformable material and comprising a cosmetically eye enhancing material, the at least one dynamic fluid zone being configured to interact with eyelids such that blinking causes the cosmetically eye enhancing material to move thereby reflecting light in a dynamic manner.

In accordance with still another aspect, the present invention is directed to an ophthalmic device. The device comprising a contact lens having an optic region, a peripheral region surrounding the optic region, a front surface and a back surface and requiring rotational stability on eye, at least one dynamic fluid zone incorporated into the contact lens between the front surface and the back surface in the peripheral region, the at least one dynamic fluid zone being formed from a deformable material and comprising at least one of a therapeutic, a nutritional, and a pharmacological agent for delivery to an eye of a patient through one or more openings, the at least one dynamic fluid zone being configured to interact with the eyelids such that blinking causes movement of the at least one of a therapeutic, a nutritional, and a pharmacological agent, and at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material, and wherein the eyelids make an angle of contact with the at least one dynamic stabilization zone that changes when the eyelids move across the at least one dynamic stabilization zone, the at least one dynamic stabilization zone also comprising a cosmetically eye enhancing material, the at least one dynamic stabilization zone being configured to interact with the eyelids such that blinking causes the cosmetically eye enhancing material to move thereby reflecting light in a dynamic manner.

In accordance with yet another aspect, the present invention is directed to an ophthalmic device. The device comprising a contact lens having an optic region, a peripheral region surrounding the optic region, a front surface and a back surface and requiring rotational stability on eye, at least one first dynamic fluid zone incorporated into the contact lens between the front surface and the back surface in the peripheral region, the at least one first dynamic fluid zone being formed from a deformable material and comprising at least one of a therapeutic, a nutritional, and a pharmacological agent for delivery to an eye of a patient through one or more openings, the at least one first dynamic fluid zone being configured to interact with the eyelids such that blinking causes movement of the at least one of a therapeutic, a nutritional, and a pharmacological agent, at least one second dynamic fluid zone incorporated into the contact lens between the front surface and the back surface in the peripheral region, the at least one second dynamic fluid zone being formed from a deformable material and comprising a cosmetically eye enhancing material, the at least one second dynamic fluid zone being configured to interact with eyelids such that blinking causes the cosmetically eye enhancing material to move thereby reflecting light in a dynamic manner, and at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material at eye temperature, and wherein the eyelids make an angle of contact with the at least one dynamic stabilization zone that changes when the eyelids move across the at least one dynamic stabilization zone.

In accordance with still yet another aspect, the present invention is directed to an ophthalmic device. The device comprising a corrective lens having an optic region, a peripheral region surrounding the optic region, a front surface and a back surface, and at least one dynamic fluid zone incorporated into the contact lens between the front surface and the back surface in the peripheral region, the at least one dynamic fluid zone being formed from a deformable material and comprising a cosmetically eye enhancing material, the at least one dynamic fluid zone including a protrusion being configured to interact with the upper eyelid such that blinking causes the cosmetically eye enhancing material to move in a wavelike manner through the at least one dynamic fluid zone.

In accordance with yet another aspect, the present invention is directed to an ophthalmic device. The device comprising a corrective lens having an optic region, a peripheral region surrounding the optic region, a front surface and a back surface, and at least one dynamic fluid zone incorporated into the contact lens between the front surface and the back surface in the peripheral region, the at least one dynamic fluid zone comprising a cosmetically eye enhancing material that reflects light based upon internally generated stimulus.

In accordance with yet another aspect, the present invention is directed to an ophthalmic device. The device comprising a contact lens having an optic region, a peripheral region surrounding the optic region, a front surface and a back surface and requiring rotational stability on eye, and at least one dynamic stabilization zone incorporated into the contact lens, the at least one dynamic stabilization zone being configured to facilitate alignment, via rotation, of the contact lens on the eye at a rotational angle for optimal placement of rotationally asymmetric limbal ring patterns and comprising a deformable material, and wherein the eyelids make an angle of contact with the at least one dynamic stabilization zone that changes when the eyelids move across the at least one dynamic stabilization zone, the at least one dynamic stabilization zone also comprising a cosmetically eye enhancing material, the at least one dynamic stabilization zone being configured to interact with the eyelids such that blinking causes the cosmetically eye enhancing material to move thereby reflecting light in a dynamic manner.

Contact lenses or contacts are simply lenses placed on the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeabilities and are generally more comfortable to wear than the contact lenses made of the earlier hard materials.

Currently available contact lenses remain a cost effective means for vision correction. The thin plastic lenses fit over the cornea of the eye to correct vision defects, including myopia or nearsightedness, hyperopia or farsightedness, astigmatism, i.e. asphericity in the cornea, and presbyopia i.e. the loss of the ability of the crystalline lens to accommodate. Contact lenses are available in a variety of forms and are made of a variety of materials to provide different functionality. Daily wear soft contact lenses are typically made from soft polymer materials combined with water for oxygen permeability. Daily wear soft contact lenses may be daily disposable or extended wear disposable. Daily disposable contact lenses are usually worn for a single day and then thrown away, while extended wear disposable contact lenses are usually worn for a period of up to thirty days. Colored soft contact lenses use different materials to provide different functionality. For example, a visibility tint contact lens uses a light tint to aid the wearer in locating a dropped contact lens, enhancement tint contact lenses have a translucent tint that is meant to enhance one's natural eye color, the color tint contact lens comprises a darker, opaque tint meant to change one's eye color, and the light filtering tint contact lens functions to enhance certain colors while muting others. Rigid gas permeable hard contact lenses are made from siloxane-containing polymers but are more rigid than soft contact lenses and thus hold their shape and are more durable. Bifocal contact lenses are designed specifically for patients with presbyopia and are available in both soft and rigid varieties. Toric contact lenses are designed specifically for patients with astigmatism and are also available in both soft and rigid varieties. Combination lenses combining different aspects of the above are also available, for example, hybrid contact lenses.

The present invention utilizes dynamic fluid or gel zones positioned between the front and the back surfaces of a contact lens, or intraocular lens, corneal inlay or onlay. Upon interacting with the upper and lower eyelids, these fluid zones may be deformed such that the resulting deformation may be leveraged to provide rotational stability, to transport/pump fluids/materials from a reservoir to the eye, to agitate fluid/materials contained in a reservoir, or to various combinations and/or permutations of any of the different functions described herein. In a first embodiment, as the material in the zones deforms, the angle of contact between the eyelids and the zones changes as does the rotational force acting on the contact lens. In a second embodiment, one or more fluid zones may comprise an agent to be delivered to the eye. In one physical realization of this embodiment, two fluid zones not linked to one another, but having the ability to interact with each other to achieve movement of an agent contained in a reservoir, under eyelid pressure, may move an agent out of the reservoir and onto the eye. In a second realization of this embodiment, multiple fluid zones, some of which may be in fluid communication with each other for transport of fluid from a central reservoir to or towards an outlet port or second reservoir, under eyelid pressure, and thus eventually onto the surface of the eye. In a third embodiment, a single fluid zone may comprise reflective and/or tinted particles. The geometry of this single fluid zone may be configured such that upon blinking, a dynamic response of the fluid zone results in the fluid and any particles contained therein to be agitated and thus cause movement, i.e. shimmer. Multiple fluid zones each containing reflective particles may also be utilized to achieve different dynamic cosmetic effects upon interaction with the eyelids.

The contact lens incorporating the dynamic fluid zone is relatively simple to design and manufacture. The contact lens incorporating the dynamic fluid zone is also relatively inexpensive to manufacture as compared to currently manufactured contact lenses. In other words, the incorporation of dynamic fluid zones does not require a significant increase in manufacturing cost.

While focused on ocular applications, specifically contact lenses, it is recognized that the present invention may be utilized in other areas of the body.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Figure 1:
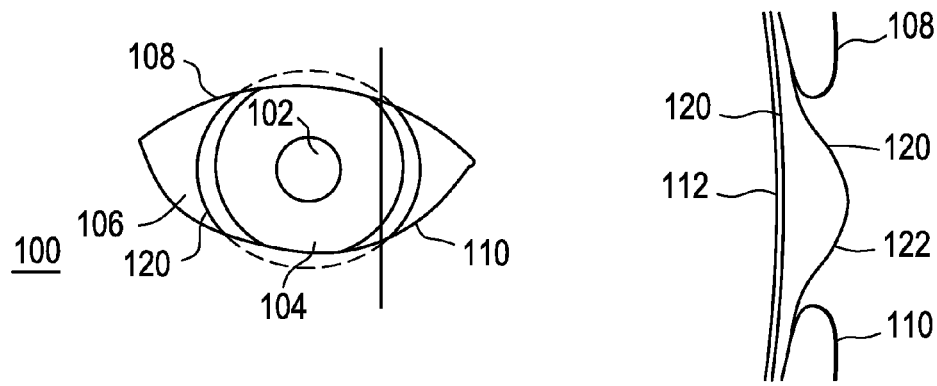
FIG. 1 is a diagrammatic representation of a prior art contact lens having an eyelid stabilized design feature in planar and cross sectional views.

Currently, contact lenses requiring rotational stabilization in order to maintain optimal visual acuity, for example, toric contact lenses, rely on either weight or eyelid pressure to maintain the contact lens oriented on the eye. Referring to FIG. 1, there is illustrated in both plan and cross-sectional view an eyelid pressure stabilized design wherein the contact lens 120 is thicker in a stabilization zone or region 122. The contact lens 120 is positioned on the eye 100 such that it covers the pupil 102, the iris 104 and a portion of the sclera 106 and sits under both the upper and lower eyelids 108 and 110 respectively. The thicker stabilization zone 122 in this design is positioned over the cornea 112. Once stabilized, the stabilization zone 122 is maintained between the upper and lower eyelids 108 and 110.

Figure 2:
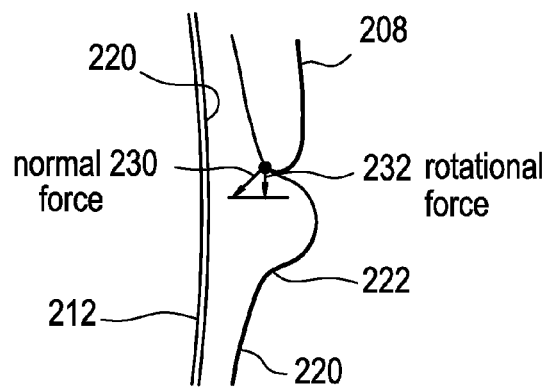
FIG. 2 is a detailed diagrammatic representation of the interaction zone between the upper eyelid and the contact lens of FIG. 1.

FIG. 2 illustrates in greater detail how the thicker stabilization zone 222 interacts with the upper eyelid 208 to induce a force that tends to rotate the contact lens 220. The critical parameter driving this rotational force is the angle of the contact area between the upper eyelid 208 and the stabilization zone 222 of the contact lens 220. As illustrated, the normal force, represented by vector 230, at a point of contact between the upper eyelid 208 and the periphery of the thicker stabilization zone 222 may be resolved into a rotational force, represented by vector 232. The steeper the angle of the stabilization zone 222, the greater the rotational force component of the normal force acting on the contact lens 220. Conversely, the lower or flatter the angle of the stabilization zone 222, the lower the rotational force component of the normal force acting on the contact lens 220.

The dynamic fluid zones of the present invention, as set forth above may be utilized for a number of functions. In the stabilization function, the dynamic fluid zones are referred to as dynamic stabilization zones, whereas in the other functions, they are simply referred to as dynamic fluid or gel zones.

In accordance with the present invention, the dynamic stabilization zone or zones may preferably be filled with a substance that may redistribute when pressure is applied. Essentially, the present invention is directed to a contact lens incorporating one or more dynamic stabilization zones that comprise a material that create one or more dynamic stabilization zones having varying physical properties. In one exemplary embodiment, as is described in greater detail subsequently, the contact lens comprises one or more fluid or gel filled cavities forming dynamic stabilization zones. When the force or pressure from the eyelids compresses the edge of the one or more dynamic stabilization zones, the fluid or gel preferably redistributes with the cavity or cavities, thereby causing the one or more dynamic stabilization zones to change shape. More specifically, the increased pressure from the eyelids causes the local shape of the one or more stabilization zones at the eyelid contact point to increase thereby causing a larger rotational force than with a fixed shape stabilization zone or zones. As the eyelid movement continues, for example during a blink, this change in shape will result in a steepening of the angle of contact and thereby deliver more rotational force to the contact lens. In other words, as the eyelids continue to pass over the one or more dynamic stabilization zones, the fluid or gel continues to redistribute and the surface slopes continue to change. It may be possible with advanced modeling techniques to design dynamic stabilization zone(s) that provides both improved rotational speed upon insertion (auto-positioning) and increased stability of the contact lens when it is in position.

Figure 3A:
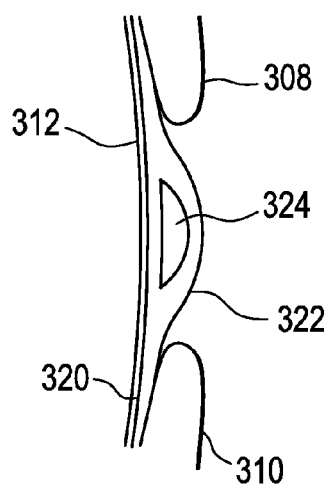
FIGS. 3A, 3B and 3C are diagrammatic representations of the progressive change in shape of a dynamic stabilization zone as a function of eyelid movement in accordance with the present invention.
Figure 3B:
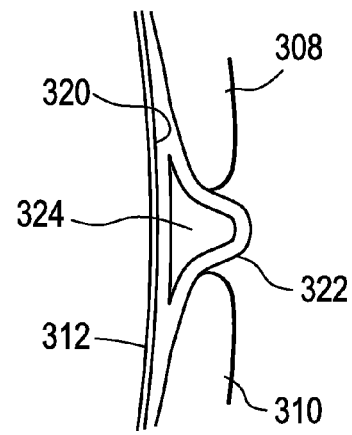
Figure 3C:
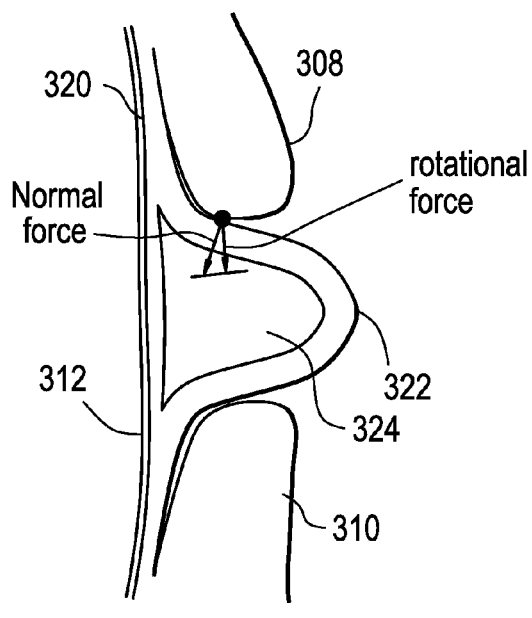

Referring to FIGS. 3A, 3B and 3C, there is illustrated the change in shape of a single dynamic stabilization zone as a function of eyelid movement over the contact lens. Although one or more dynamic stabilization zones may be utilized in a single contact lens, for ease of explanation only a single dynamic stabilization zone is described. FIG. 3A illustrates the position of the dynamic stabilization zone 322 of the contact lens 320 prior to blinking or eyelid movement. As illustrated, the eyelids 308 and 310 are positioned over the contact lens 320, but are not in contact with the dynamic stabilization zone 322 and thus have not caused any redistribution of the fluid or gel 324 within the cavity defining the dynamic stabilization zone 322. FIG. 3B illustrates the altered position (steeper angle) of the dynamic stabilization zone 322 during a blink. As the eyelids 308 and 310 converge, the pressure therefrom causes the fluid or gel 324 in the cavity defining the dynamic stabilization zone 322 to redistribute, thereby increasing the angle of the dynamic stabilization zone 322. FIG. 3C illustrates the further altered position of the dynamic stabilization zone 322 as the eyelids 308 and 310 continue to converge during blinking. As may be readily discerned from FIG. 3C, the steeper the angle of the dynamic stabilization zone 322, the closer the rotational force represented by vector 332 comes to the normal force represented by vector 330 which in turn indicates a greater proportion of the normal force is translated or resolved to rotational force acting on the contact lens 320.

Figure 4:
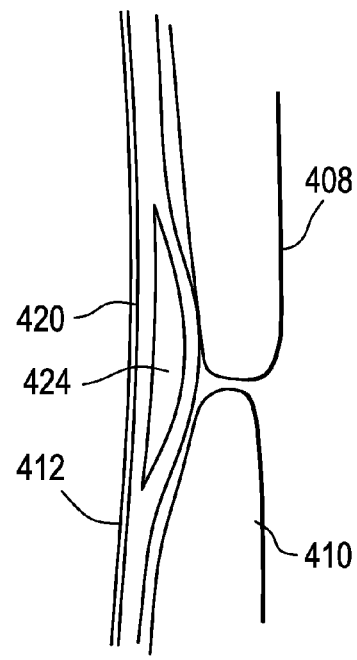
FIG. 4 is a diagrammatic representation of the dynamic stabilization zone with the upper and lower eyelids in full blink position in accordance with the present invention.

In addition to better rotational stability of the contact lens due to increased rotational force imparted by the eyelids, the dynamic stabilization zone design of the present invention preferably increases wearer comfort. Referring to FIG. 4, as full blink is achieved and the eyelids 408 and 410 pass over substantially the entire dynamic stabilization zone 422, the fluid or gel 424 within the cavity defining the dynamic stabilization zone 422 will once again redistribute due to the pressure exerted by the eyelids 408 and 410 into a flatter configuration. This flatter configuration allows the eyelids 408 and 410 to pass over the contact lens 420 with less downwardly directed force on the eye since the maximum thickness has been reduced due to the redistribution. Fixed stabilization zones do not thin out and thus may be less comfortable due to increased interaction with the eyelids passing over the contact lens.

As set forth herein, the contact lens of the present invention may comprise one or more dynamic stabilization zones. These one or more dynamic stabilization zones may comprise any suitable configuration and may be positioned at any suitable location on the contact lens to meet any number of design requirements. It is important to note, however, that in configuring any design that the upper and lower eyelids do not move strictly in a vertical direction, with an up down stroke during blinking. The upper eyelid moves substantially vertically, with a small nasal component during blinking, and the lower eyelid moves substantially horizontally, moving nasal ward during blinking with only a slight or small vertical movement. Additionally, the upper and lower eyelids are not symmetrical with respect to a plane cutting though the vertical meridian. In other words, individuals do not blink symmetrically relative to a horizontal axis drawn between the open upper and lower lid. Also, it is known that the eyes converge when the viewer gazes down.

Figure 5:
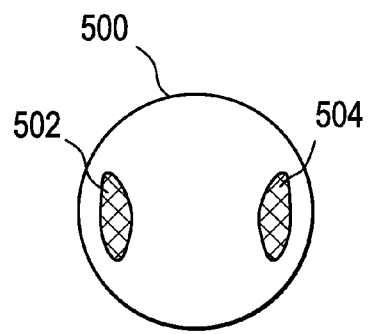
FIG. 5 is a diagrammatic representation of a first exemplary contact lens in accordance with the present invention.
Figure 6:
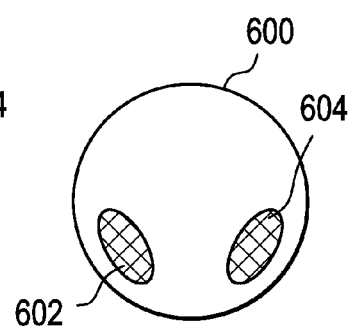
FIG. 6 is a diagrammatic representation of a second exemplary contact lens in accordance with the present invention.
Figure 7:
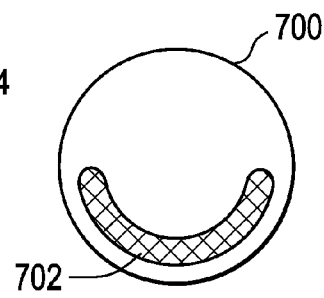
FIG. 7 is a diagrammatic representation of a third exemplary contact lens in accordance with the present invention.

FIG. 5 illustrates an exemplary embodiment of a contact lens 500 comprising two dynamic stabilization zones 502 and 504. In this exemplary embodiment, the fluid or gel filled cavities forming the dynamic stabilization zone 502 and 504 are positioned symmetrically about the horizontal axis of the contact lens 500 and about one hundred eighty degrees apart from one another. FIG. 6 illustrates another exemplary embodiment of a contact lens 600 also comprising two dynamic stabilization zones 602 and 604. In this exemplary embodiment, the fluid or gel filled cavities forming the dynamic stabilization zones 602 and 604 are shifted downwardly off the horizontal axis of the contact lens 600 and less than one hundred eighty degrees apart from one another as measured below the horizontal axis. This configuration utilizes gravity in combination with eyelid pressure to orient and maintain orientation of the contact lens 600 on the eye. FIG. 7 illustrates yet another exemplary embodiment of a contact lens 700 comprising a single dynamic stabilization zone 702. In this exemplary embodiment, the fluid or gel filled cavity forming the single dynamic stabilization zone 702 is formed in the lower region of the contact lens 700 such that gravity as well as eyelid pressure and/or eyelid movement operates on the contact lens 700 similarly to a prism ballast contact lens.

While each of these exemplary embodiments may be utilized in accordance with the present invention, it is important to note that any number of dynamic stabilization zone configurations may be utilized as long as the dynamic stabilization zones contain or are fabricated from a moveable or flowable material that changes shape when the eyelid passes over the dynamic stabilization zone, and their shape and placement are determined by taking into account eyelid movement as briefly described above. Non-symmetric designs, different designs for the left and right eyes, or custom stabilization designs for a given eye are possible with the dynamic stabilization zones of the present invention. In addition, custom contact lenses, for example, contact lenses fabricated directly from eye measurements, may incorporate dynamic stabilization zones in accordance with the present invention. Independent of the configuration, shape and placement of the dynamic stabilization zones on the contact lens is the ability of the material forming these or within these dynamic stabilization zones to redistribute itself under the pressure of eyelid movement that makes the present invention work.

The material or materials utilized to form a dynamic stabilization zone may comprise any suitable biocompatible material or materials that offer the desired mechanical properties. The material or materials should preferably be readily deformable under the pressure of eyelid movement as well as oxygen permeable so that the one or more dynamic stabilization zones on a contact lens do not substantially interfere with the eye receiving needed oxygen. The one or more dynamic stabilization zones in accordance with the present invention may be incorporated into any number of contact lenses, including those formed from silicone hydrogels, as long as the material or materials forming the one or more dynamic stabilization zones is both chemically and physically compatible with the material or materials forming the contact lens. With respect to physical compatibility, the material or materials forming the contact lens preferably does not allow the material or materials forming a dynamic stabilization zone, for example, a fluid or gel, to permeate and/or otherwise diffuse or leak from the cavity formed in the contact lens to secure the dynamic stabilization zone. With respect to chemical compatibility, the material or materials forming a dynamic stabilization zone preferably does not react in any manner with the material or materials forming the contact lens and/or the eye. The material or materials forming a dynamic stabilization zone may be positioned or secured in a cavity and/or space formed in the correct region of the contact lens in any suitable manner as discussed in greater detail subsequently.

The material or materials forming a dynamic stabilization zone may comprise any suitable biocompatible and deformable material having a glass transition temperature of less than about thirty-four degrees C.

Silicone based materials for forming the one or more dynamic stabilization zones may be preferable in that silicone based materials, including silicone oils, have the desired mechanical properties or may be easily tailored to have the desired mechanical properties to enable the invention. Silicone based materials, including silicone oils, are also highly oxygen permeable. In addition, many soft contact lenses are formed from silicone based materials and as such would be compatible. Fluorosilicone based materials may also be utilized.

In alternate exemplary embodiments, the material or materials for forming the one or more dynamic stabilization zones may comprise the same material or materials forming the contact lens. In another alternate exemplary embodiment, the material or materials for forming the one or more dynamic stabilization zones may be in a solid, liquid or gas state. In yet another alternate exemplary embodiment, the material or materials for forming the one or more dynamic stabilization zones may be in one form or state during the manufacturing process and in another form or state when place on the eye. For example, the material or materials for forming the one or more dynamic stabilization zones may be solid or frozen during the manufacturing process and in liquid form thereafter. In still another alternate exemplary embodiment, the material or materials forming the one or more dynamic stabilization zones may be a self contained material or combination of materials that may be incorporated directly into a cavity of the contact lens or it may be a material or combination of materials that preferably have to be encapsulated or otherwise protected prior to being incorporated into a cavity of the contact lens.

Figure 8:
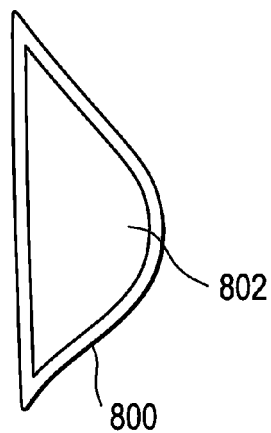
FIG. 8 is a diagrammatic representation of an exemplary dynamic zone capsule for a contact lens in accordance with the present invention.

As set forth above, the contact lens comprising one or more dynamic stabilization zones of the present invention may be manufactured utilizing any number of processes. In one exemplary embodiment, the one or more dynamic stabilization zones may be formed into capsules with a flexible outer material and pre-filled with the fluid or gel before being positioned in the contact lens. Some possible methods of manufacturing the capsules include welding, for example by heat or ultrasonically, two portions of film to form the top and bottom and injecting the fluid or gel before completing the seal around the edge. The film may comprise any suitable material, including those described above. FIG. 8 illustrates an exemplary embodiment of a capsule 800 with the fluid or gel 802 contained therein. The shape of the exemplary capsule 800 is arbitrary and only represents one possible design. A similar process, as set forth above, is to use a material for the one or more stabilization zones that may be positioned in the contact lens while frozen, but is liquid at eye temperatures. These pre-made fluid regions would preferably be placed into the contact lens molds with the contact lens raw material and bonded or encapsulated in the contact lens as the contact lens is cured.

In the exemplary embodiment wherein a space and/or cavity is created in the contact lens for the formation of a dynamic stabilization zone, the space and/or cavity may be created in a manner similar to that of the manufacture of a hybrid contact lens. For example, in this exemplary process, a liquid reactive monomer mixture predose is applied to a front curve and then the deformable material in the desired form is applied thereto. Once the deformable material is accurately positioned in the desired location, the monomer is pre-cured to a specified amount to facilitate release of the mechanical fixturing device while maintaining positional accuracy. Finally, the remainder of the monomer is added, the back curve positioned and the entire assembly is cured.

Figure 9:
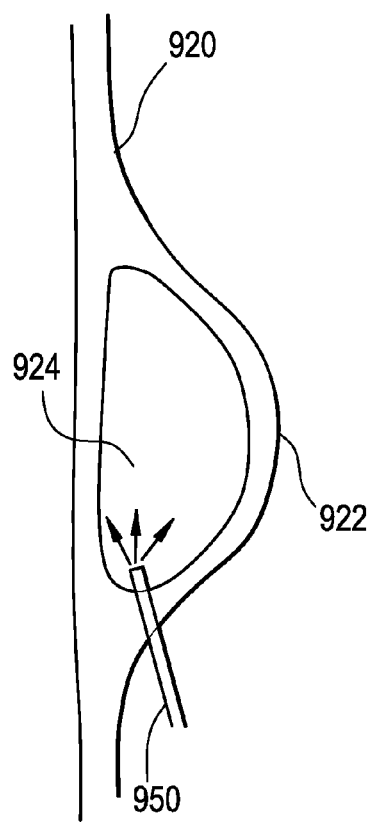
FIG. 9 is a diagrammatic representation of an exemplary process for fabricating a contact lens incorporating one or more dynamic stabilization zones in accordance with the present invention.

In accordance with another exemplary embodiment, the contact lens may be fabricated utilizing known processes then injected directly with the fluid or gel utilizing a needle or similar device. Essentially, the one or more dynamic stabilization zone cavities would be formed by injecting the material directly into the contact lens at the desired location(s). FIG. 9 illustrates a needle 950 inserted into the contact lens 920 to create a dynamic stabilization zone 922 with a fluid or gel 924 injected via the needle 950. Once the material is injected and the needle removed, the hole at the insertion site may be sealed. In one exemplary embodiment, the injection hole may be sealed as part of the curing process. For example, the injection of the material may be done before the contact lens is fully cured and final cure would take place after removing the needle, allowing the uncured material to close the hole and then cure it closed.

In accordance with yet another exemplary embodiment, a process wherein contact lens material may be cured from the outside in, and by controlled curing on both sides may be utilized to create a thick region of un-cured or under-cured material, i.e. different crosslink density, may thus be trapped, thereby forming the one or more dynamic stabilization zones.

In accordance with yet another exemplary embodiment, a contact lens may be manufactured utilizing rotationally-symmetric contact lens molds, as if for a sphere product, while utilizing multiple curable formulations that, when cured, differ in their abilities to absorb water, in their elastic modulus, and in their monomer composition. For example, it is well-known to those of skill in the relevant art that curable contact lens formulations may be made more hydrophilic by way of incorporation of higher concentrations of monomers with greater affinity for water, for example, methacrylic acid. Furthermore, curable contact lens formulations may be adjusted to achieve a desired hydrated modulus by varying the amounts and/or types of crosslinking agents for example, ethylene glycol dimethacrylate.

In accordance with still another exemplary embodiment, one or more dynamic stabilization zones may be realized by pad printing certain patterns onto a front curve during the contact lens fabrication process. In one exemplary embodiment, a printable dynamic stabilization zone composition may be formulated to achieve relatively high equilibrium water content, for example, greater than sixty-five (65) percent and/or a relatively low modulus, for example, less than seventy (70) psi. It is also known to those of skill in the relevant art that the expansion factor (defined herein by as-processed lens volume divided by as-cured lens volume) of a liquid curable monomer mixture may be adjusted by adding or subtracting non-reactive diluents. Specifically, by reducing the diluent level, the expansion factor is increased. By increasing the diluent level, the expansion factor is reduced. Useful curable compositions for printing dynamic stabilization zones could utilize curable monomer mixtures having a relatively low diluent level, thereby resulting in localized zones that will absorb more water and protrude from the front surface of the contact lens. With appropriate formulation of a low diluent content liquid curable monomer mixture to achieve relatively high equilibrium water content, a relatively low elastic modulus, and a suitable pad printing viscosity and volatility, a dynamic stabilization zone pattern may be printed onto a front surface contact lens mold having utility according to the present invention. When fully processed, a contact lens having such a feature would be comprised of at least two distinct curable monomer formulations. Furthermore, the resulting contact lens would have proud dynamic stabilization zones comprising hydrogel material that differs in composition, for example, water content, monomer content, and/or crosslink density, from the bulk of the contact lens. Accordingly, in such an exemplary embodiment, the one or more dynamic stabilization zones are not fluid-filled sacs, rather, they are discrete viscoelastic zones having tailored chemical and physical properties.

In the case where stabilization zones are pad printed onto a front curve with tailored curable liquid monomer mixtures, the composition of the mixture should be such that it will co-polymerize with the material that is used in the bulk of the contact lens. In this manner, the printed dynamic stabilization zone is chemically bonded to the bulk of the contact lens, and such zones are processable in a similar manner to the bulk material of the contact lens.

Contact lenses, intraocular lenses as well as any number of medical devices may be utilized for the local delivery of therapeutic agent/therapeutic agent combinations to treat a wide variety of conditions or to enhance the function and/or life of the medical device itself. Other medical devices which often fail due to tissue in-growth or accumulation of proteinaceous material in, on and around the device, such as shunts for hydrocephalus, dialysis grafts, colostomy bag attachment devices, ear drainage tubes, leads for pace makers and implantable defibrillators may also benefit from the device-therapeutic agent combination approach. Devices which serve to improve the structure and function of tissue or organ may also show benefits when combined with the appropriate therapeutic agent or agents. For example, improved osteointegration of orthopedic devices to enhance stabilization of the implanted device could potentially be achieved by combining it with agents such as bone-morphogenic protein. Similarly other surgical devices, sutures, staples, anastomosis devices, vertebral disks, bone pins, suture anchors, hemostatic barriers, clamps, screws, plates, clips, vascular implants, tissue adhesives and sealants, tissue scaffolds, various types of dressings, bone substitutes, intraluminal devices, and vascular supports could also provide enhanced patient benefit using this therapeutic agent-device combination approach. Essentially, any type of medical device may be coated in some fashion with or contain therein a therapeutic agent or therapeutic agent combination which enhances treatment over use of the singular use of the medical device or pharmaceutical agent.

The various medical devices set forth above or any medical device in general may be coated with or contain one or more therapeutic agents for local delivery and tailored for a specific purpose, for example, prevention of a condition, treatment of a condition, mitigation of a condition and/or the enhancement of the medical device function. These therapeutic agents include anti-proliferative/antimitotic agents including natural products such as vinca alkaloids (i.e. vinblastine, vincristine, and vinorelbine), paclitaxel, epipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozotocin), dacarbazine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents; anti-inflammatory agents, such as adrenocortical steroids (cortisol, cortisone, fludrocortisone, prednisone, prednisolone, 6α-methyl-prednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, and phenylbutazone), nabumetone, gold compounds (auranofin, aurothioglucose, gold sodium thiomalate); immunosuppresives, cyclosporine, tacrolimus (FK-506), sirolimus (rapamycin), azathioprine, mycophenolate mofetil; angiogenic agents: vascular endothelial growth factor (VEGF), fibroblast growth factor (FGF); angiotensin receptor blockers; nitric oxide donors; antisense oligonucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

The present invention utilizes dynamic fluid or gel zones incorporated into ocular devices such as contact lenses, intraocular lenses, corneal inlays and/or onlays. Upon interacting with the upper and lower eyelids, these fluid zones may be deformed such that the resulting deformation may be leveraged to either agitate fluid/materials contained in a reservoir, or transport/pump fluids formulated from a reservoir into or onto the eye.

In accordance with another exemplary embodiment, the stabilization zones described herein may be reconfigured as dynamic fluid zones. In other words, rather than, or in addition to, the dynamic fluid zones may be utilized as stabilization zones for contact lenses requiring rotational stability, as described above, as well as for delivering therapeutic agents to the eye and/or to create a cosmetic effect via dynamic eye enhancement. Each use may be combined or utilized individually as is explained above.

In one exemplary embodiment, the dynamic fluid zones may be utilized to deliver a therapeutic, nutritional or pharmacological agent. Depending on the application, the dynamic fluid zones may comprise a single active pharmaceutical ingredient or multiple active pharmaceutical ingredients. Examples of therapies that may be accomplished utilizing contact lenses to deliver agents include, providing ocular nutrition, treating glaucoma, treating allergies, mitigating myopia progression, treating dry eye, and delivering antibiotics, analgesics, anti-fungals, anti-virals, anti-infectives, mydriatics and cycloplegics, and anti-inflammatory agents. With respect to ocular nutrition, the dynamic fluid zones of the contact lens may be utilized to deliver vitamins, antioxidants and nutraceuticals including vitamins A, D and E, lutein, taurine, glutathione, zeaxanthin, fatty acids and other similar agents. With respect to treating glaucoma, the dynamic fluid zones of the contact lens may be utilized to deliver agents for one or more of the treatment, inhibition and prevention of glaucoma, including epinephrines such as dipivefrin, alpha-2 adrenergic receptors such as aproclonidine and brimonidine, betablockers such as betaxolol, carteolol, levobunolol, metipranolol and timolol, direct miotics such as carbachol and pilocarpine, cholinesterase inhibitors such as physostigmine and echothiophate, carbonic anhydrase inhibitors such as acetazolamide, brinzolamide, dorzolamide and methazolamide, prostoglandins and prostamides such as latanoprost, bimatoprost, uravoprost, travoprost, and unoprostone cidofovir. With respect to treating allergies, the dynamic fluid zones of the contact lens may be utilized to deliver a number of agents including azelastine HCl, emedastine difumarate, epinastine HCl, ketotifen fumarate, levocabastine HCl, olopatadine HCl, pheniramine maleate and antazoline phosphate for one or more of the treatment, inhibition and prevention of allergies. With respect to delivering antibiotics and anti-infectives, the dynamic fluid zones of the contact lens may be utilized to deliver agents including tobramycin, moxifloxacin, ofloxacin, gatifloxacin, ciprofloxacin, gentamicin, sulfisoxazole diolamine, sodium sulfacetamide, vancomycin, polymyxin B, amikacin, norfloxacin, levofloxacin, sulfisoxazole diolamine, sodium sulfacetamide tetracycline, doxycycline, dicloxacillin, cephalexin, amoxicillin/clavulante, ceftriaxone, cefixime, erythromycin, ofloxacin, azithromycin, gentamicin, sulfadiazine and pyrimethamine. With respect to delivering anti-virals, the dynamic fluid zones of the contact lens may be utilized to deliver agents including fomivirsen sodium, foscarnet sodium, ganciclovir sodium valganciclovir HCl, trifluridine, acyclovir and famciclovir. With respect to delivering anti-fungals, the dynamic fluid zones of the contact lens may be utilized to deliver agents including fluconazole, flucytosine, amphotericin B, itraconazole and ketoconazole. With respect to delivering analgesics, the dynamic fluid zones of the contact lens may be utilized to deliver agents including acetaminophen and codeine, acetaminophen and hydrocodone, acetaminophen, ketorolac, ibuprofen and tramadol. With respect to delivering mydriatics and cycloplegics, the dynamic fluid zones of the contact lens may be utilized to deliver agents including atropine sulfate, homatropine, scopolamine HBr, cyclopentolate HCl, tropicamide and phenylephrine HCl. With respect to delivering anti-inflammatories, the dynamic fluid zones of the contact lens may be utilized to deliver corticosteriods, including dexamethasone sodium phosphate, dexamethasone, fluoromethalone, fluoromethalone acetate, loteprednol etabonate, prednisolone acetate, prednisolone sodium phosphate, medrysone, rimexolone and fluocinolone acetonide as well as non-steroidal anti-inflammatory agents, including flurbiprofen sodium, suprofen, diclofenac sodium, ketorolac, tromethamine, cyclosporine, rapamycin methotrexate, azathioprine and bromocriptine. With respect to mitigating myopia progression, the dynamic fluid zones of the contact lens may be utilized to deliver metered doses of pirenzepene or atropine. This may be utilized in of itself as a means for treating myopia progression or it may be utilized in combination with an optical zone design of the contact lens specifically for myopia mitigation.

The active agents delivered by the contact lenses may be formulated to comprise carriers or excipients. Any number of excipients may be utilized, including synthetic and natural polymers, for example, polyvinylalcohol, polyethyleneglycol, polyacrylic acid, hydroxymethyl cellulose, glycerine, hypromellose, polyvinylpyrrolidone, carbopol, propyleneglycol, hydroxypropyl guar, glucam-20, hydroxypropyl cellulose, sorbitol, dextrose, polysorbate, mannitol, dextran, modified polysaccharides and gums, phosolipids and sulphobetaines.

The one or more therapeutic agents may be delivered from the contact lens in a number of ways. In the above described exemplary embodiments, the dynamic stabilizations zone or zones may be filled with a substance that redistributes when pressure is applied by the eyelids. These dynamic stabilization zones are incorporated into the contact lens outside of the optic zone. In accordance with the present invention, dynamic fluid zones are incorporated into the contact lens outside of the optic zone and may perform a number of nonexclusive functions, including dynamic stabilization, drug delivery and/or cosmetic dynamic eye enhancement. In one exemplary embodiment, a first fluid zone may surround a second fluid zone such that deformation of the first fluid zone causes pressure on the second zone which in turn causes the contents i.e. one or more therapeutic agents, to be expelled therefrom. The one or more therapeutic agents may be expelled through pores in the material forming the second fluid zone, for example, a weeping design, or through a valve mechanism. In an alternate exemplary embodiment, there may be multiple second fluid zones communicating with one another as well as multiple first fluid zones. The placement of each of these zones may correspond to any suitable location as described above. In addition, the first fluid zones may comprise the same or similar structure as the dynamic stabilization zones described above and illustrated herein.

In a preferred exemplary embodiment, a central reservoir comprising one or more therapeutic, nutritional or pharmacological agents, hereafter referred to as an agent or agents may be positioned at a suitable location in the peripheral zone or stabilization zone of a contact lens. Upon blinking, the agent contained within this central reservoir would preferably be pumped in small increments through a chain of fluid filled sacs and/or reservoirs, thereby metering the flow of the one or more agents onto the eye. Depending on the number and type of reservoirs and valve mechanisms utilized, one may tailor the flow/delivery of the one or more agents to achieve the derived therapeutic effect, i.e. burst delivery of the one or more agents, sustained delivery of the one or more agents and/or something in between burst and sustained delivery. This chain arrangement or fluid sacs and/or reservoirs provide for a regulated flow of the agent which takes into account the normal human blink rate of about four (4) to eight (8) blinks per minute.

Figure 10A:
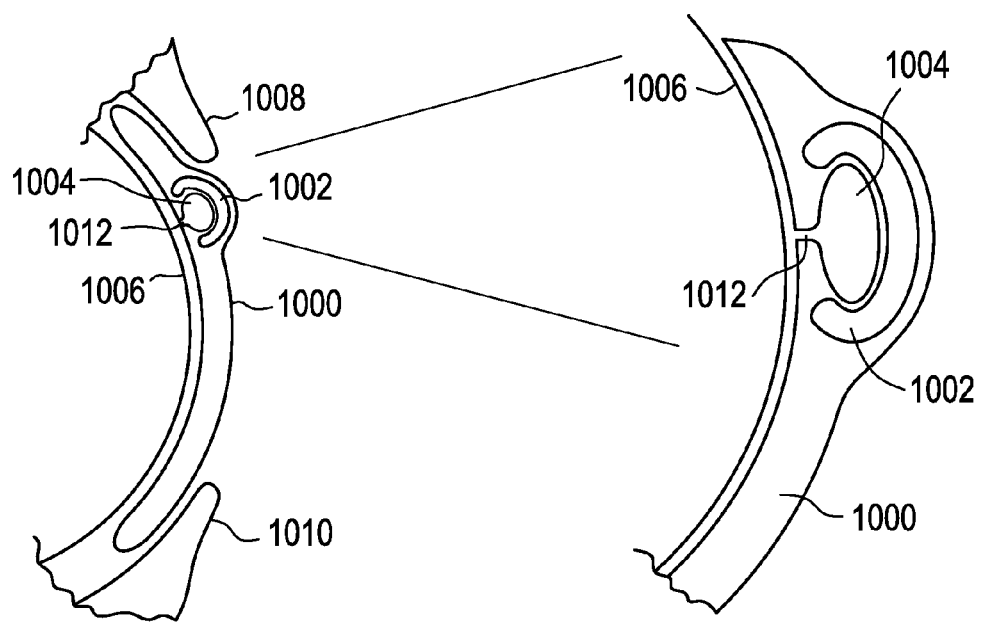
FIGS. 10A and 10B are diagrammatic representations of a first exemplary embodiment of a dynamic fluid zone for the delivery of an agent to the eye in accordance with the present invention.
Figure 10B:
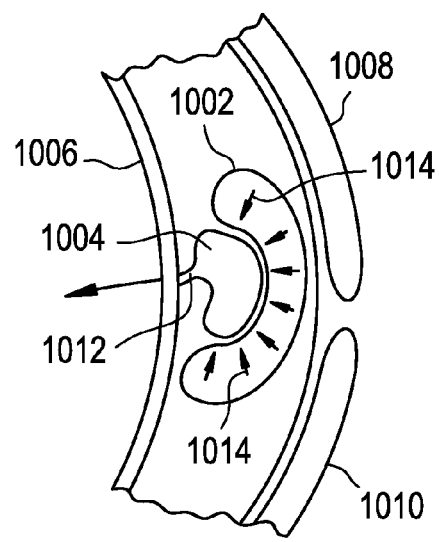

Referring now to FIGS. 10A and 10B, there is illustrated a cross-sectional view of the exemplary embodiment wherein a first fluid zone surrounds a second fluid zone. FIG. 10A illustrates a contact lens 1000 having at least one set of fluid zones 1002, 1004 positioned on the cornea 1006 and sitting partially under the eyelids 1008 and 1010, and FIG. 10B illustrates the same contact lens 1000 with the eyelids 1008 and 1010 closed over the contact lens 1010 in full blink. As illustrated, a fluid filled sac 1002 incorporated into the contact lens 1000 substantially surrounds a sac or reservoir 1004 comprising the one or more agents. The fluid filled sac 1002 may comprise any suitable fluid and may be formed as described herein with respect to the dynamic stabilization zones. In addition to exerting pressure on the agent reservoir 1004, it may act as a stabilization zone. The agent reservoir 1004 may be formed in a similar manner as the fluid filled sac 1002 but comprises at least one agent to be released into or onto the eye. The at least one agent may comprise any suitable material as described above and any other material for treating a condition as described in detail above. As the agent reservoir 1004 is designed to release one or more agents, it preferably comprises a release mechanism 1012. The release mechanism 1012 may comprise any suitable means for allowing the one or more agents to pass from the reservoir 1004 when the eyelids 1008 and 1010 exert pressure on the fluid filled sac 1002 which in turn causes pressure on the agent reservoir 1004 as shown by arrows 1014. In one exemplary embodiment, the release mechanism 1012 may comprise a single one-way check valve formed from the same material as the sacs 1002 and 1004; however, any suitable material may be utilized. In an alternate exemplary embodiment, the release mechanism 1012 may simply comprise pores in the reservoir 1004 that allow the one or more agents to pass through when the fluid filled sac 1002 is deformed by the eyelids 1008 and 1010 but prevent fluid from the eye from entering the reservoir 1004.

Figure 10C:
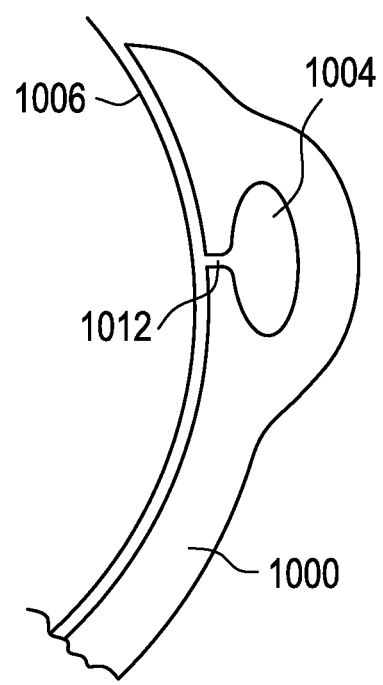
FIG. 10C is a diagrammatic representation of a second exemplary embodiment of a dynamic fluid zone for the delivery of an agent to the eye in accordance with the present invention.

In an alternate exemplary embodiment, the present invention may be realized with just a reservoir. FIG. 10C illustrates a contact lens 1000 comprising an agent containing reservoir 1004 and a release mechanism 1012. As in the above described exemplary embodiment, blinking forces the agent onto the eye; however, it is directly rather than via the fluid filled sac 1002 illustrated in FIGS. 10A and 10B. Each time the wearer blinks, agent is released into or onto the eye. Unlike the previous exemplary embodiment, when the reservoir 1004 is empty, the contact lens 1000 no longer comprises any fluid filled sac.

Figure 11:
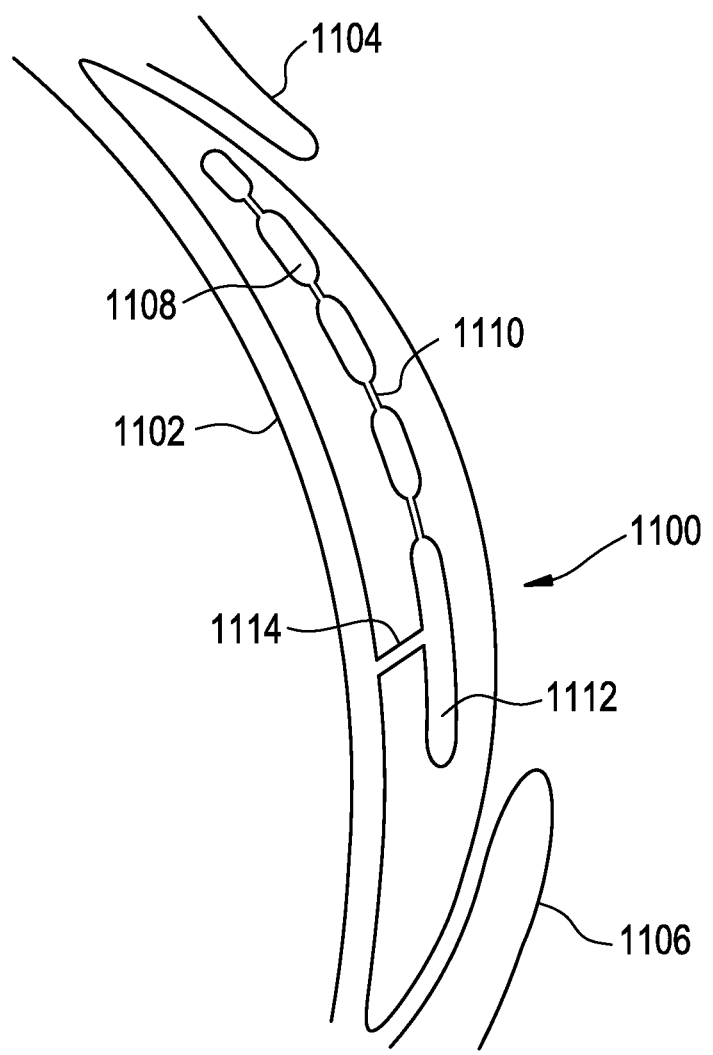
FIG. 11 is a diagrammatic representation of a third exemplary embodiment of a dynamic fluid zone for the delivery of an agent to the eye in accordance with the present invention.

FIG. 11 illustrates a cross-sectional view of the exemplary embodiment wherein a central reservoir which includes multiple linked smaller reservoirs. As illustrated, a contact lens 1100 which sits on the eye 1102 and partially under the eyelids 1104 and 1106 comprises a series of agent filled reservoirs 1108 fluidly connected via valve mechanisms 1110. When a person blinks, the eyelids 1104 and 1106 come together and force the at least one agent in the reservoirs 1108 towards a central reservoir 1112 which comprises a release mechanism 1114. Each successive blink causes the at least one agent contained in the reservoirs 1108 to move towards the central reservoir 1112 through the valves 1110 until a certain point is reached such that the next blink causes the at least one agent to be released through the release mechanism 1114. As a person blinks at a rate of about four (4) to eight (8) blinks per minute, the dose rate of the at least one aspect may be controlled via a number of factors including reservoir 1108/1112 size and agent viscosity.

The valves 1110 and release mechanism 1114 may comprise any suitable means for allowing one way fluid flow, including check valves as described above. However, any suitable means may be utilized.

In accordance with another exemplary embodiment, one or more dynamic fluid zones may be incorporated into a contact lens such that the pressure exerted by the eyelids on these one or more dynamic fluid zones causes a dynamic response with the fluid and/or particles contained therein. In other words, the geometry of the one or more fluid zones and the materials contained therein may achieve, upon blinking, a dynamic response of the one or more fluid zones resulting in the fluid/particles contained therein to be agitated and thus cause movement, i.e. shimmer. Small reflective or shiny particles, for example, helicones, which may be suspended within the fluid of a closed system or reservoir, e.g. a dynamic fluid zone, would be agitated by the action of the eyelids passing over them. This would cause the fluid and the particles to move about or around, creating a sparkling, glittering or shimmering appearance on the eye. This could be enabled by placing fragments of a reflective material within the fluid zone and adjusting the viscosity of the fluid to tailor the extent/duration of the effect. Suitable materials for the particles may comprise any suitable materials, including mica chip fragments, pieces of helicone liquid crystals, and the like. The fluid may comprise any suitable material, including siloxane-containing oils, such as silicone oil or similar fluids. Silicone oil is any of cyclized, oligomerized or polymerized siloxanes bearing organic functional groups. In this exemplary embodiment, it is preferred that if multiple dynamic fluid zones are utilized in a single lens that they are each a closed system and do not communicate with each other. These dynamic fluid zones may be preferantially located depending on the desired effects. For example, the dynamic fluid zone may be positioned to correspond to the limbal ring. Recent studies have suggested that limbal rings have an effect on individuals when an individual is being judged on attractiveness. Accordingly, the dynamic fluid zone may be utilized to enhance a limbal ring. Alternately, an interesting cosmetic effect may be achieved by mixing objects or materials into the fluid in the reservoirs which exhibit rainbow like or multi-spectral effects. This may result in an effect similar to the interference effects seen in thin films such as soap bubbles or oil slicks. Accordingly, mixtures of surfactants, oils, or thin film inclusions may be added or incorporated into the fluid in the reservoir and the effect would be similar to a moving or shimmering rainbow. For example, the reservoir may be filled with a liquid having at least one thin film layer thereon.

In alternate exemplary embodiments, various other materials may be utilized to achieve different effects. For example, luminescent, phosphorescent and/or fluorescent materials may be added to provide a desired effect. Interference pigments may also be utilized. Interference pigments may comprise various substrates coated with thin films of a high refractive index substance, for example titanium dioxide coated mica. Interference pigments are utilized in a wide range of applications, including cosmetics. Any of these materials may be utilized alone or in combination with any of the materials described herein. Regardless of the materials utilized, additional effects may be achieved by varying the fluid properties, for example, viscosity.

Figure 12A:
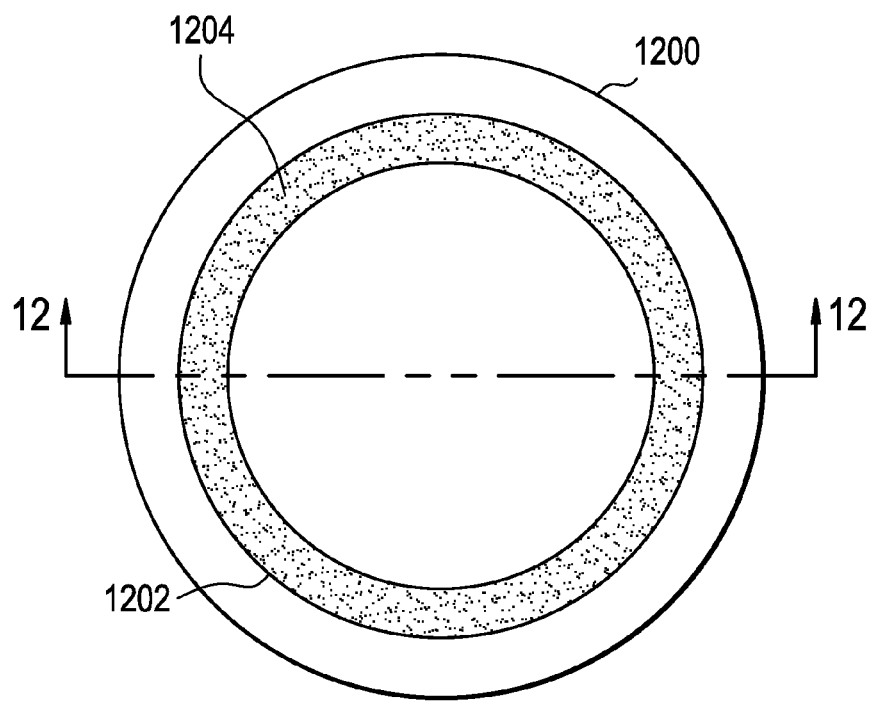
FIGS. 12A and 12B are diagrammatic representations of a first exemplary embodiment of a dynamic fluid zone configured as a cosmetic enhancement reservoir in accordance with the present invention.
Figure 12B:
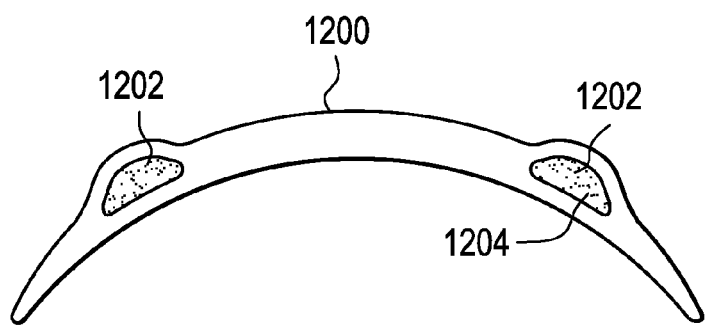

Referring now to FIGS. 12A and B, there is illustrated a plan and cross-sectional view a contact lens 1200 comprising a single dynamic fluid zone 1202 configured as a ring outside of the optic zone of the contact lens 1200. The dynamic fluid zone 1202 comprises a fluid filled reservoir containing particles 1204 as described above. As the eyelids pass over the dynamic fluid zone 1202, the particles 1204 are distorted and move. This movement may cosmetically enhance the appearance of the eye as set forth in detail above. It is important to note that although a single, continuous ring is illustrated, the dynamic fluid zone of the present invention may be implemented utilizing any number of discrete segments. In addition, the dynamic fluid zone may comprise any suitable shape and configuration.

Figure 13:
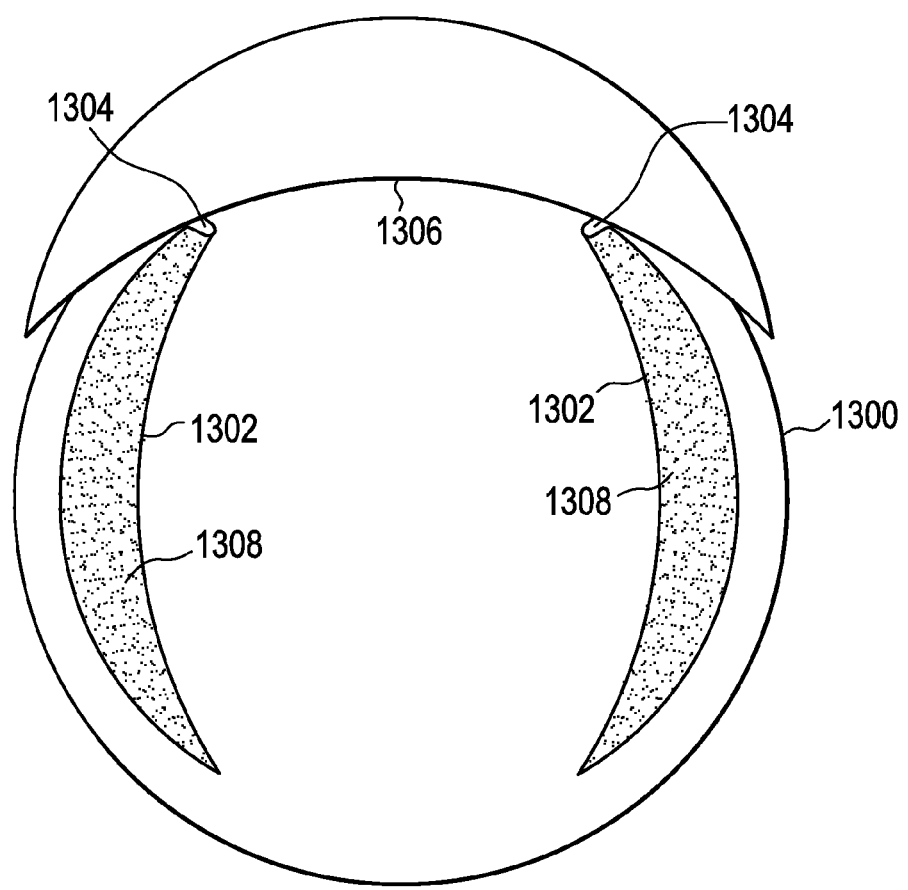
FIG. 13 is a diagrammatic representation of a second exemplary embodiment of a dynamic fluid zone configured as a cosmetic enhancement reservoir in accordance with the present invention.

FIG. 13 illustrates a plan view of a contact lens 1300 comprising two dynamic fluid zones 1302, each having a substantially crescent shape. In this exemplary embodiment, the dynamic fluid zones 1302 comprises a design feature 1304 as the superior margins of the fluid zones 1302 that interact with the upper eyelid 1306 during a blink. This interaction results in a wavefront in each fluid zone 1302 causing the embedded or suspended particles 1308 to become agitated and thereby reflect light in a dynamic fashion. This exemplary embodiment may comprise any number of dynamic fluid zones. It is important to note that a wavefront may be started with or without design features built in just by simply by blinking and the selection of the proper fluids.

In each of the above described exemplary embodiments, the dynamic fluid zones are raised surfaces on the contact lenses in order that they interact with the eyelids. In the case of eye enhancement, the fluid and particles or materials contained therein maybe incorporated into regions of the contact lens without raised surfaces so that there is little to no interaction with the eyelids. In this configuration, the dynamics or movement of the material or particles would not be caused by interaction with the eyelids, but through other factors, including eye movement, head movement, body heat and any other function that may cause movement. In other words, the cosmetically eye enhancing material reflects light based upon internally generated stimulus or stimulus generated by the wearer.

As set forth above, the various exemplary embodiments may be combined in any number of permutations. For example, one or more fluid zones may be utilized just for agent delivery or for eye enhancement. In other exemplary embodiments, the one or more fluid zones may be utilized for providing rotational stability and drug delivery, for providing rotational stability and eye enhancement, and for providing rotational stability, drug delivery and eye enhancement. In addition to the permutations set forth herein, a further combination may be possible. Current limbal ring designs are generally rotationally symmetric and thus rotational positioning is not an issue. However, as one considers the potential of rotationally asymmetric designs, for example, oval or elliptical shapes, or placement of various effects at fixed, non-rotationally aligned positions, rotational alignment of the contact lens on the eye becomes a factor. As a factor, it is preferably controlled otherwise the intended pattern or effect therefrom may not be achieved Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic device comprising:
   a corrective lens having an optic region, a peripheral region surrounding the optic region, a front surface and a back surface;
   at least one dynamic fluid zone incorporated into the corrective lens between the front surface and the back surface in the peripheral region, the at least one dynamic fluid zone being formed from a deformable material and comprising at least one of a therapeutic, a nutritional, and a pharmacological agent for delivery to an eye of a patient through one or more openings, the one or more openings comprises a valve configured to allow one way fluid flow, the at least one dynamic fluid zone being configured to interact with the eyelids such that blinking causes movement of the at least one of a therapeutic, a nutritional, and a pharmacological agent and
   at least one second dynamic fluid zone incorporated into the contact lens between the front surface and the back surface in the peripheral region, wherein the at least one second fluid dynamic zone substantially surrounds the at least one dynamic fluid zone and comprises a deformable material, wherein the at least one second dynamic fluid zone is configured to compress the at least one dynamic fluid zone under eyelid pressure during blinking thereby forcing the at least one of a therapeutic, a nutritional and a pharmacological agent from the at least one dynamic fluid zone onto the eye.

2. The ophthalmic device according to claim 1, wherein the corrective lens is a contact lens.

3. The ophthalmic device according to claim 2, wherein the contact lens comprises a soft contact lens.

4. The ophthalmic device according to claim 2, wherein the contact lens comprises a toric contact lens.

5. The ophthalmic device according to claim 1, wherein the at least one dynamic fluid zone comprises one or more peripheral reservoirs and a central reservoir, the one or more peripheral reservoirs and the central reservoir being connected to and in fluid communication with one another via one-way valves.

6. The ophthalmic device according to claim 5, wherein the one or more peripheral reservoirs are configured to compress under eyelid pressure during blinking thereby forcing the at least one of a therapeutic, a nutritional and a pharmacological agent from one peripheral reservoir to another peripheral reservoir to the central reservoir.

7. The ophthalmic device according to claim 6, wherein the central reservoir is configured to compress under eyelid pressure during blinking thereby forcing the at least one of a therapeutic, a nutritional and a pharmacological agent supplied from the one or more peripheral reservoirs to the eye.

8. The ophthalmic device according to claim 5, wherein one or more openings are positioned in the central reservoir and comprise a valve configured to allow one way fluid flow.

9. An ophthalmic device comprising:
   a contact lens having an optic region, a peripheral region surrounding the optic region, a front surface and a back surface and requiring rotational stability on eye;
   at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material at eye temperature, and wherein the eyelids make an angle of contact with the at least one dynamic stabilization zone that changes when the eyelids move across the at least one dynamic stabilization zone;
   at least one dynamic fluid zone incorporated into the contact lens between the front surface and the back surface in the peripheral region, the at least one dynamic fluid zone being formed from a deformable material and comprising at least one of a therapeutic, a nutritional, and a pharmacological agent for delivery to an eye of a patient through one or more openings, the one or more openings comprises a valve configured to allow one way fluid flow the at least one dynamic fluid zone being configured to interact with the eyelids such that blinking causes movement of the at least one of a therapeutic, a nutritional, and a pharmacological agent; and
   at least one second dynamic fluid zone incorporated into the contact lens between the front surface and the back surface in the peripheral region, wherein the at least one second fluid dynamic zone substantially surrounds the at least one dynamic fluid zone and comprises a deformable material, wherein the at least one second dynamic fluid zone is configured to compress the at least one dynamic fluid zone under eyelid pressure during blinking thereby forcing the at least one of a therapeutic, a nutritional and a pharmacological agent from the at least one dynamic fluid zone onto the eye.

10. The ophthalmic device according to claim 9, wherein the corrective lens is a contact lens.

11. The ophthalmic device according to claim 10, wherein the contact lens comprises a soft contact lens.

12. The ophthalmic device according to claim 10, wherein the contact lens comprises a toric contact lens.

13. The ophthalmic device according to claim 9, wherein the angle of contact between the eyelids and the at least one dynamic stabilization zone increases during blinking thereby increasing the rotational force acting on the contact lens until the eyelids are substantially in contact with one another thereby flattening the deformable material in the at least one dynamic stabilization zone.

14. The ophthalmic device according to claim 9, wherein the deformable material comprises a biocompatible liquid at eye temperature.

15. The ophthalmic device according to claim 9, wherein the deformable material comprises a biocompatible gel at eye temperature.

16. The ophthalmic device according to claim 9, wherein the deformable material comprises a biocompatible gas at eye temperature.

17. The ophthalmic device according to claim 9, wherein the at least one dynamic fluid zone comprises one or more peripheral reservoirs and a central reservoir, the one or more peripheral reservoirs and the central reservoir being connected to and in fluid communication with one another via one-way valves.

18. The ophthalmic device according to claim 17, wherein the one or more peripheral reservoirs are configured to compress under eyelid pressure during blinking thereby forcing the at least one of a therapeutic, a nutritional and a pharmacological agent from one peripheral reservoir to another peripheral reservoir to the central reservoir.

19. The ophthalmic device according to claim 18, wherein the central reservoir is configured to compress under eyelid pressure during blinking thereby forcing the at least one of a therapeutic, a nutritional and a pharmacological agent supplied from the one or more peripheral reservoirs to the eye.

20. The ophthalmic device according to claim 19, wherein one or more openings are positioned in the central reservoir and comprise a valve configured to allow one way fluid flow.

21. An ophthalmic device comprising:
a contact lens having an optic region, a peripheral region surrounding the optic region, a front surface and a back surface and requiring rotational stability on eye; and
at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material, and wherein the eyelids make an angle of contact with the at least one dynamic stabilization zone that changes when the eyelids move across the at least one dynamic stabilization zone, the at least one dynamic stabilization zone also comprising a cosmetically eye enhancing material, the cosmetically eye enhancing material comprises a fluid and particles, the fluid comprises silicone oils and surfactants and the particles comprises helicone liquid crystals the at least one dynamic stabilization zone being configured to interact with the eyelids such that blinking causes the cosmetically eye enhancing material to move thereby reflecting light in a dynamic manner.

22. The ophthalmic device according to claim 21, wherein the corrective lens is a contact lens.

23. The ophthalmic device according to claim 22, wherein the contact lens comprises a soft contact lens.

24. The ophthalmic device according to claim 22, wherein the contact lens comprises a toric contact lens.

25. The ophthalmic device according to claim 21, wherein the angle of contact between the eyelids and the at least one dynamic stabilization zone increases during blinking thereby increasing the rotational force acting on the contact lens until the eyelids are substantially in contact with one another thereby flattening the deformable material in the at least one dynamic stabilization zone.

26. The ophthalmic device according to claim 21, wherein the deformable material comprises a biocompatible liquid at eye temperature.

27. The ophthalmic device according to claim 21, wherein the deformable material comprises a biocompatible gel at eye temperature.

28. The ophthalmic device according to claim 21, wherein the deformable material comprises a biocompatible gas at eye temperature.

29. The ophthalmic device according to claim 21, wherein the fluid further comprises oils.

30. The ophthalmic device according to claim 21, wherein the fluid further comprises a liquid having at least one thin film layer thereon.

31. An ophthalmic device comprising:
a contact lens having an optic region, a peripheral region surrounding the optic region, a front surface and a back surface and requiring rotational stability on eye;
at least one dynamic stabilization zone incorporated into the contact lens, the at least one dynamic stabilization zone being configured to facilitate alignment, via rotation, of the contact lens on the eye at a rotational angle for optimal visual acuity and comprising a deformable material at eye temperature, and wherein the eyelids make an angle of contact with the at least one dynamic stabilization zone that changes when the eyelids move across the at least one dynamic stabilization zone; and
at least one dynamic fluid zone incorporated into the contact lens between the front surface and the back surface in the peripheral region, the at least one dynamic fluid zone being formed from a deformable material and comprising a cosmetically eye enhancing material, the cosmetically eye enhancing material comprises a fluid and particles, the fluid comprises silicone oils and surfactants and the particles comprises helicone liquid crystals the at least one dynamic fluid zone being configured to interact with eyelids such that blinking causes the cosmetically eye enhancing material to move thereby reflecting light in a dynamic manner.

32. The ophthalmic device according to claim 31, wherein the corrective lens is a contact lens.

33. The ophthalmic device according to claim 32, wherein the contact lens comprises a soft contact lens.

34. The ophthalmic device according to claim 32, wherein the contact lens comprises a toric contact lens.

35. The ophthalmic device according to claim 31, wherein the angle of contact between the eyelids and the at least one dynamic stabilization zone increases during blinking thereby increasing the rotational force acting on the contact lens until the eyelids are substantially in contact with one another thereby flattening the deformable material in the at least one dynamic stabilization zone.

36. The ophthalmic device according to claim 31, wherein the deformable material comprises a biocompatible liquid at eye temperature.

37. The ophthalmic device according to claim 31, wherein the deformable material comprises a biocompatible gel at eye temperature.

38. The ophthalmic device according to claim 31, wherein the deformable material comprises a biocompatible gas at eye temperature.

39. The ophthalmic device according to claim 31, wherein the at least one dynamic fluid zone comprises a reservoir for the cosmetically eye enhancing material.

40. The ophthalmic device according to claim 31, wherein the fluid further comprises oils.

41. The ophthalmic device according to claim 31, wherein the fluid further comprises a liquid having at least one thin film layer thereon.

* * * * *